(12) United States Patent
Fulton et al.

(10) Patent No.: US 8,124,028 B2
(45) Date of Patent: Feb. 28, 2012

(54) AUTOMATED LIQUID HANDLING DEVICE AND ASSOCIATED ASSAY UNIT

(75) Inventors: Scott P. Fulton, Middleton, WI (US); Robert J. Sakowski, Barneveld, WI (US)

(73) Assignee: Agilent Technologies, Inc., Loveland, CO (US)

( * ) Notice: Subject to any disclaimer, the term of this patent is extended or adjusted under 35 U.S.C. 154(b) by 0 days.

(21) Appl. No.: 12/808,833

(22) PCT Filed: Dec. 19, 2008

(86) PCT No.: PCT/US2008/087744
§ 371 (c)(1),
(2), (4) Date: Jul. 21, 2010

(87) PCT Pub. No.: WO2009/079661
PCT Pub. Date: Jun. 25, 2009

(65) Prior Publication Data
US 2011/0020919 A1    Jan. 27, 2011

Related U.S. Application Data

(63) Continuation-in-part of application No. 11/188,535, filed on Jul. 25, 2005, now Pat. No. 7,799,279.

(60) Provisional application No. 61/014,967, filed on Dec. 19, 2007.

(51) Int. Cl.
*C12Q 1/68* (2006.01)
*B01L 3/00* (2006.01)
*B01L 3/02* (2006.01)
*G01N 1/18* (2006.01)
*G01N 1/10* (2006.01)

(52) U.S. Cl. .......... 422/501; 422/50; 422/514; 436/177; 436/180

(58) Field of Classification Search .......... 422/410, 422/50, 501, 514; 436/177, 180
See application file for complete search history.

(56) References Cited

U.S. PATENT DOCUMENTS 5,057,281 A    10/1991  Torti et al.
5,827,744 A *  10/1998  Fose et al. .............. 436/49
(Continued)

FOREIGN PATENT DOCUMENTS
WO    WO 2004/007081 A1    1/2004

OTHER PUBLICATIONS

Kopaciewicz et al.; Aluminum ion mediated stabilization of the silica-based anion-exchange packings to caustic regenerants, *Journal of Chromatography*, 503:385-401 (1990).

*Primary Examiner* — Jill Warden
*Assistant Examiner* — Dean Kwak

(57) ABSTRACT

The present invention provides a novel system for efficiently and accurately analyzing targets in samples and for preparing samples for analysis with various analytical methods. A version of the present invention comprises a multi-function probe, configured for pipetting liquids directly, with a pipet tip, or with an assay unit described herein. Another version of the present invention includes an apparatus for conducting an immunoassay or selective adsorption separation comprising an assay unit and a multi-function probe. Another version of the present invention includes a multi-function probe and assay unit for use with an automated Cartesian robot. Other versions include one- or two-dimensional arrays comprising multi-function probes connected to syringe barrels for use with assay units.

19 Claims, 6 Drawing Sheets

U.S. PATENT DOCUMENTS

| | | |
|---|---|---|
| 6,732,574 B2 | 5/2004 | Hajduk et al. |
| 6,761,855 B1 | 7/2004 | Cook et al. |
| 6,889,727 B2 | 5/2005 | Olson et al. |
| 7,001,774 B1 | 2/2006 | Gamble et al. |
| 2005/0019951 A1* | 1/2005 | Gjerde et al. ................. 436/177 |
| 2006/0019407 A1 | 1/2006 | Fulton et al. |
| 2007/0251341 A1* | 11/2007 | Balmer ............................ 74/49 |
| 2008/0156117 A1 | 7/2008 | Londo et al. |

* cited by examiner

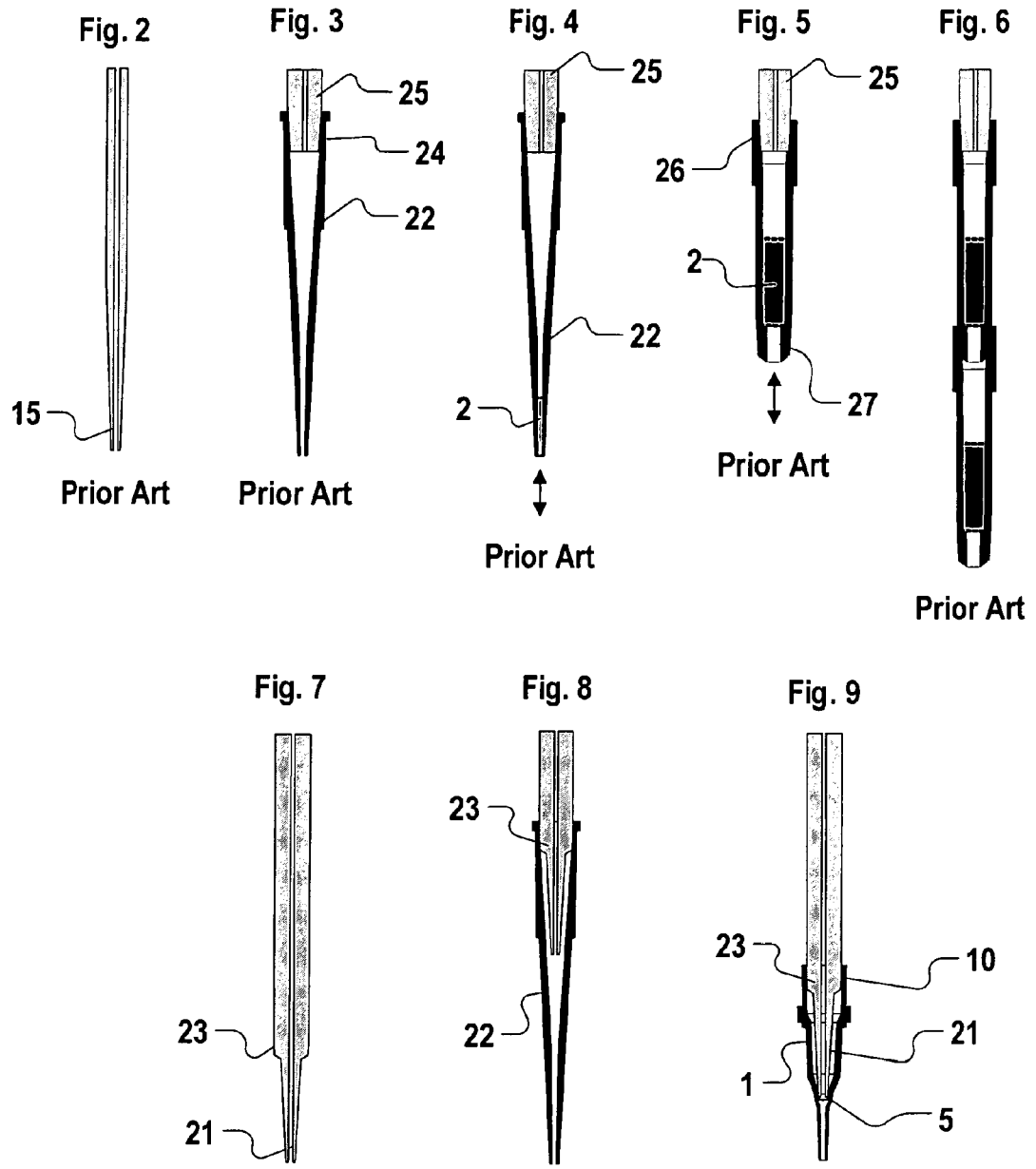

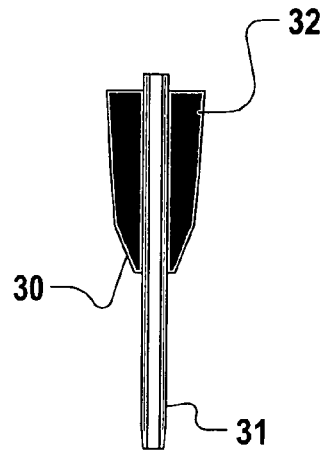
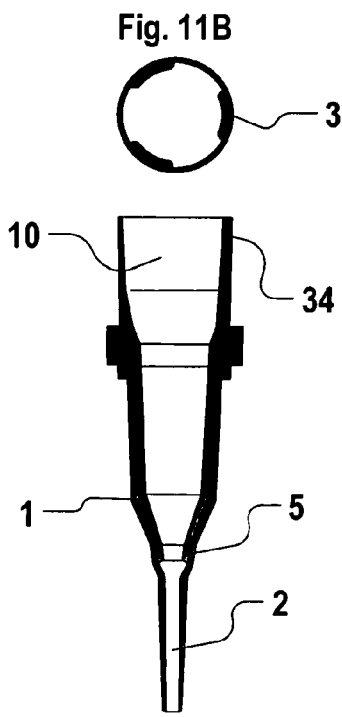
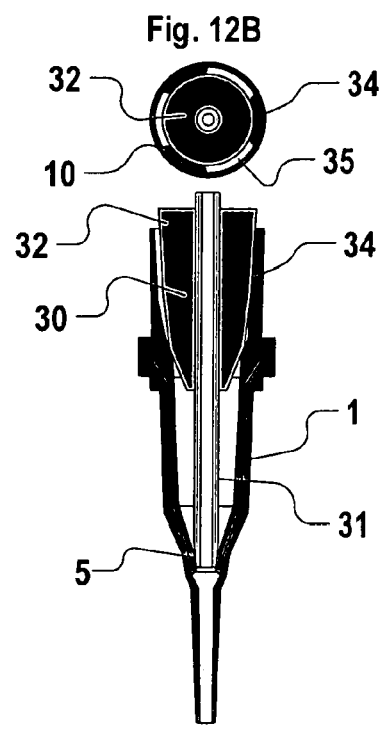
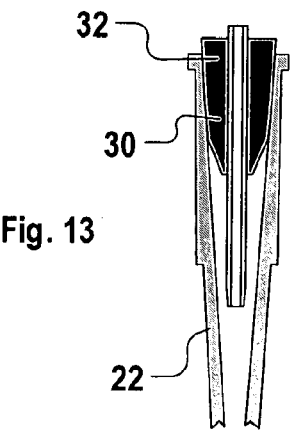
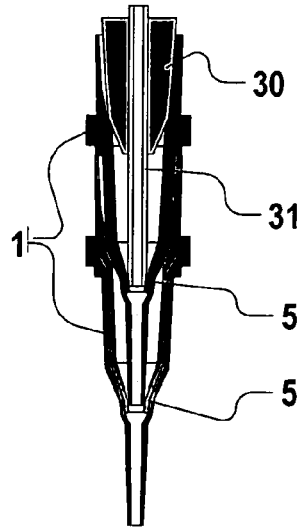

Side View

Top View

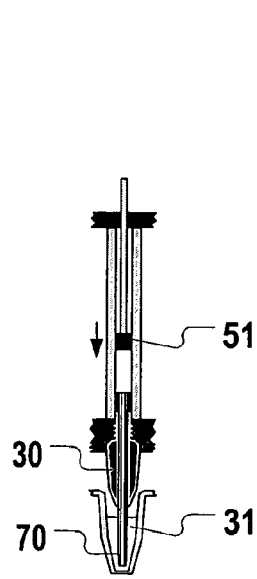
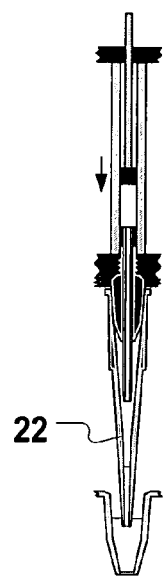
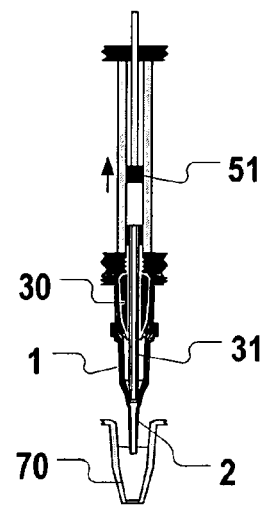
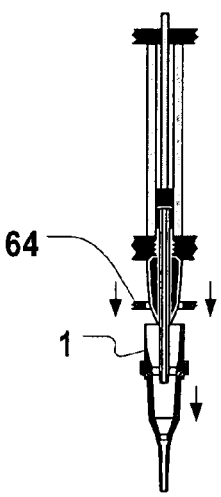
Fig. 21  Fig. 22  Fig. 23  Fig. 24
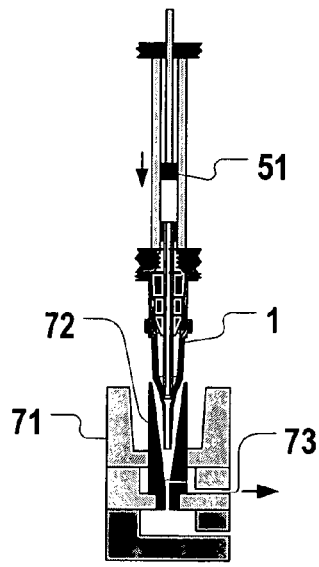
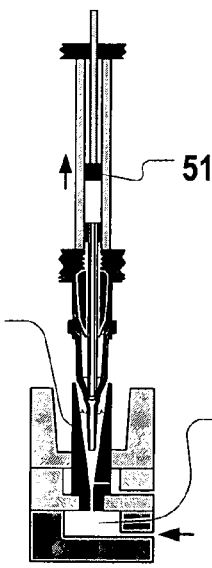
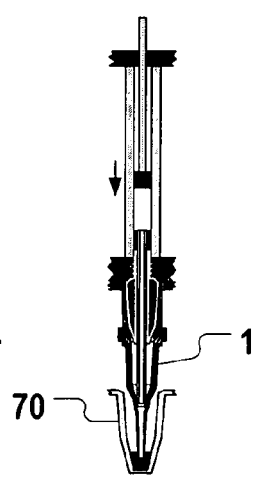
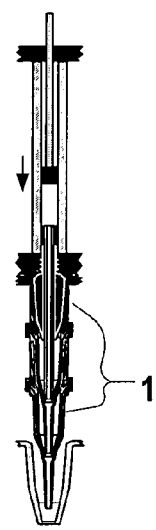
Fig. 25  Fig. 26  Fig. 27  Fig. 28

AUTOMATED LIQUID HANDLING DEVICE AND ASSOCIATED ASSAY UNIT

CROSS-REFERENCE TO RELATED APPLICATIONS

This application is a continuation-in-part of U.S. patent application Ser. No. 11/188,535, filed Jul. 25, 2005 now U.S. Pat. No. 7,799,279 and claims priority to U.S. provisional patent application Ser. No. 61/014,967, filed Dec. 19, 2007, both of which incorporated herein by reference in their entirety.

FIELD OF THE INVENTION

The present invention generally relates to devices for analyzing biological samples or for preparing biological samples for analysis.

BACKGROUND OF THE INVENTION

The fields of life science research and pharmaceutical development are critically dependent upon highly selective and sensitive quantitative assays for a wide range of different biomolecules (such as proteins, antibodies, cytokines, receptors, enzymes, peptides, nucleic acids, hormones, and the like) in complex clinical or biological samples (such as blood, urine, tissue or cellular extracts, cell culture supernatants, bioprocess feedstreams, and the like). In typical samples (which may contain thousands of different molecular species) the analytes of interest may be present at extremely low concentrations (micrograms to nanograms per milliliter or less), but the samples may be available only in very small quantities (hundreds of microliters or less). The rapid growth in the field of biotechnology and the introduction of many potential new drug targets from genomic research have created an increasing demand for more rapid and efficient analytical methods, without any sacrifice in performance.

In order to simultaneously obtain high selectivity (the ability to measure one very specific molecule in a complex mixture) and high sensitivity (the ability to accurately quantify very small concentrations or amounts), a number of analytical methods have been developed which couple powerful molecular separations with extremely responsive detection methods.

One of the most widely used of these separation-based methods is the Enzyme-Linked Immuno-Sorbent Assay or ELISA. In ELISA, an antibody is immobilized on a solid phase support and exposed to a liquid sample, enabling any antigen (analytical target) to bind specifically to the antibody. Non-binding molecules in the sample are washed away. The solid phase with bound target can then be exposed to either antigen or a second antibody specific to the target that are labeled with a linked enzyme. After the non-binding labeled molecules are washed away, the solid phase is then exposed to enzyme substrate under controlled conditions so that the amount of colored or fluorescent enzyme product formed is proportional to the amount of label present, which can be used in turn to quantify the amount of target present in the original sample.

Currently in the fields of life science research and pharmaceutical development, ELISAs are done almost entirely using plastic (typically polystyrene) multi-well plates called microtiter plates or microplates. The wall of each well serves as both the solid phase for binding the antibody and antigen as well as the container for the sample and reagents that are added. Liquid addition is done by pipetting, and washing is done by rapidly pipetting a wash solution in and out of the well. Readout of the enzyme product is done through the transparent plastic wells with an optical plate reader that measures absorbance, fluorescence, or luminescence. This technique is quite simple, requires minimal specialized equipment and is very flexible in terms of the reagent systems and assay formats that can be used.

However, the microplate ELISA method suffers from a number of serious drawbacks. The most important is that the antibody is bound to the wall of the well, and thus the only way sample and reagent molecules can reach the surface to interact is by molecular diffusion. Diffusion is a relatively slow process over the potential path length of several millimeters found in a typical microplate well, and so after liquids are added for each step, the user should allow the plate to incubate for at least overnight to allow the binding reaction to approach equilibrium. Since the assay includes multiple steps, this is impractical, so incubations are typically shortened to an hour or two, meaning the binding reaction does not reach complete equilibrium. Even so, the total assay turnaround time is quite long, typically on the order of 4 to 24 hours.

In addition, microplate ELISAs are subject to a high degree of variability due to the critical techniques required. The pipetting must be done very accurately and consistently into each well. Because the binding reactions do not usually reach equilibrium, timing of pipetting between wells is critical. For the same reason, temperature variation between the inner and outer wells in a plate can lead to variability, as can jarring or vibration of the plates during incubation. Most operators are not as careful as required due to the tedium of the work, and assay coefficients of variation of 10 to 30% or more are not uncommon. Automation of microplate ELISAs using conventional liquid handling robotic equipment is possible but is quite complex and often does not improve reproducibility. Users often find that such automated assays must be constantly monitored by a human operator to prevent problems.

A related set of highly selective separations are used in a micro-preparative mode to isolate a target from a complex sample in preparation for mass spectroscopy (MS), using either an ElectroSpray Interface (ESI) or Matrix Assisted Laser Desorption Interface (MALDI) to ionize the sample upon entry into the instrument. MS is unique in its ability to very rapidly provide comprehensive identity and structural information on analyte molecules with high sensitivity from very small volumes of sample. Because of the rich structural information MS gives about individual molecular species (especially proteins), complex samples must be fractionated or at least significantly simplified to enable a meaningful MS analysis to be performed. Purification methods are also needed when the target of interest is present in very small concentrations relative to other components in the sample, as is often the case in clinical or biological samples. Once the samples are separated into individual fractions or peaks, additional processing (such as concentration, desalting, enzymatic digestion, and/or matrix addition) often must be performed to prepare the sample for analysis by the MS instrument.

In sample prep for MS, the target molecules are selectively bound to a surface by immobilized antibodies or other selective surface groups (such as ion exchange, reversed phase, hydrophobic interaction, affinity, and the like), and non-binding contaminants are washed away. Then the bound target is eluted (using for example salt, acid or organic solvent) for collection into a tube or well, or on a surface for further analytical processing. It is also possible to immobilize an enzyme (such as a protease or glycosidase) to a packed bed to enable very rapid processing of the target molecule prior to further analysis. The amounts of target analyte required for MS are very similar to those required for detection using an ELISA.

Currently two separation methods most often used in front-end preparation for MS are two-dimensional gel electrophoresis and gradient high performance liquid chromatography (HPLC). Both of these techniques are powerful and work reasonably well for comprehensively searching through all the components in complex samples. However, these methods are not without problems. Two-dimensional gels, for example, are labor-intensive, have many steps, and require many hours or even days to complete (compared to the analysis time of MS, which is usually a matter of seconds). HPLC is sometimes not compatible with large proteins, and instrumentation systems with comparable throughput can be almost as expensive and complex as the mass spectrometer itself Sample carryover can also be an issue in high-throughput applications.

Many different types of small-scale adsorption-based separation devices have been developed, and some are offered for use in MS sample preparation. Most have been adapted from devices designed for solid phase extraction (SPE) used in general analytical chemistry. SPE-type columns are often driven by a vacuum manifold, using atmospheric pressure to drive samples and eluents through the column. Another popular approach is the "spin column," in which a small packed bed is suspended in a microcentrifuge tube, with liquids driven through using a laboratory centrifuge. SPE-type columns are offered by a number of vendors in a range of common surface chemistries (normal phase, reversed phase, ion exchange, metal chelate affinity, etc.). Although they are simple, SPE columns suffer from the need to collect the final product in a test tube then transfer it by pipet to the next step in the process or to the MS interface. These sample transfer steps can lead to significant losses, especially with dilute samples. Also, most of the available spin columns are too large (typical bed volumes of 50 to 250 µL) for handling sample volumes in the low microliter range or below. It is also virtually impossible to control the flow rate through an SPE column (whether driven by vacuum or centrifugation), which can reduce capture efficiency and reproducibility.

Perhaps the most popular approach to simplifying sample preparation for MS is the use of modified pipet tips containing adsorbent materials. In the Millipore "ZIPTIP" product (Millipore Corporation, Billerica, Mass.), a standard chromatographic adsorbent is embedded in a sponge-like polymer matrix in the end of the tip. The matrix enables flow by aspiration in a standard pipettor with little pressure drop. Millipore has also made this technology available in a 96-well plate format ("ZIPPLATE") driven by a vacuum manifold, primarily for use in in-gel digestion and purification of 2D gel spots. Glygen Corp. (Columbia, Md.) has developed a tip with a flattened area at the end with the adsorbent particles embedded thermally on the inner surface. The tip can handle sample volumes as low as 1 to 10 µL. PhyNexus, Inc. (San Jose, Calif.) produces pipet tips containing affinity chromatography resins sandwiched between sealed-on screens in standard 200 and 1000 µL pipet tips. The tips produce final product in an elution volume of 10 to 15 µL.

Packed bed pipet tip devices suffer from a number of serious drawbacks. These devices move liquids through the bed by air displacement—i.e. by pulling or pushing a fixed volume of air into the tip above the bed to provide a pressure drop across the bed to induce flow. As liquid flows into or out of the tip, the air volume (and thus the pressure) changes, causing a change in the flow rate. The actual flow rate achieved can also vary because of variations in the flow resistance of the packed bed or bed support means from device to device, because of variations in the viscosity of the liquid being pumped, or because of partial plugging of the packed bed from particles in the sample.

It is also very difficult in these devices to achieve the very low flows required for complete binding, especially when affinity or antibody separations are used. As a result, multiple aspirate/dispense cycles are needed. This, in turn, leads to non-quantitative and/or non-reproducible capture of the bound target. Like SPE columns, pipet tips can only perform one separation step at a time, with some type of transfer operation required between steps and likely concomitant sample loss. Flow through the pipet tip can only go in and out through the distal port, which greatly limits the efficiency of washing and elution operations, because each aliquot of wash or elution buffer is completely mixed by the multiple aspirate/dispense steps.

A number of academic labs and companies have worked to integrate the separation and other processing steps or improve MS sensitivity through modifications to the MALDI plate itself. One example is the SELDI (Surface-Enhanced Laser Desorption Ionization) "PROTEINCHIP" product from Bio-Rad Laboratories, Inc. (Hercules, Calif.). In this approach, various surface chemistries are incorporated into a spot on the plate to cause physical adsorption, ion exchange, or separations with affinity binding using antibodies or receptors, etc. A small volume of sample is incubated on the spot. The non-binding materials washed off, and then matrix is added prior to analysis. The MALDI plate approaches are, of course, not amenable for use in electrospray MS. They are also limited to use with single binding selectivity, so that other separation and preparation steps must be carried out elsewhere. The amount of sample that can be processed in this manner is also limited, so significant concentration is difficult to achieve.

A combined system approach has been developed by Intrinsic Bioprobes, Inc. (Tempe, Ariz.). The Mass Spectrometric ImmunoAssay (MSIA) technology developed by this company uses pipet tips incorporating a porous glass frit, onto which antibodies are immobilized. The bound antigens isolated from samples are eluted onto a MALDI plate for analysis. In other products, a pipet tip antibody-based separation device (using a porous glass monolith solid phase) is used in combination with enzymes (such as trypsin) immobilized on the MALDI plate. Gyros AB (Uppsala, Sweden) has developed a microfluidic system in the form of a compact disk (CD)—shaped device that incorporates several separation steps (including antibody affinity) driven by centrifugal force. The major applications for this system are ELISA and sample preparation for MALDI MS. Bruker Daltonics, Inc. (Billerica, Mass.) has introduced the "CLINPROT" system for sample purification for MALDI MS based upon robotic liquid handling and magnetic beads.

Thus, the field of biomolecule separation is one in which there is still room for improvement to overcome some of the limitations in prior art approaches and standard equipment. In particular, the use of the microtiter plate is less appropriate today given the sensitivity and speed desired by modern analytical biochemistry.

BRIEF SUMMARY OF THE INVENTION

The present invention addresses the above-mentioned limitations in the prior art by providing a novel system for efficiently and accurately analyzing targets in samples through a variety of assays, including ELISAs, and for preparing samples for analysis with analytical methods, such as MS.

One aspect of the invention provides an assay assembly including a flow-through assay unit which interfaces with a syringe pump through a probe.

In another aspect, the invention provides a flow-through assay unit having a packed particle bed; a pair of bed supports; a frustum-shaped inlet sealing surface immediately above the packed bed; and a vented, frustum-shaped opening above the inlet sealing surface.

In another aspect, the flow-through unit of the invention is releasably attached to a probe on a liquid handling device, forming a fluid-tight connection between the probe and the packed bed.

In another aspect, the invention provides a probe on a liquid handling device having a needle or tube designed both for directly aspirating or dispensing small volumes of liquids and for connecting to the inlet sealing surface of the assay unit. It also provides a hub designed both to seal to a standard disposable pipet tip and to provide a friction fit on the vented opening of the flow-through assay unit.

In another aspect, the probe is connected either directly or via tubing to a syringe pump to aspirate or dispense fluids through the probe and/or flow-through assay unit at a precisely controlled flow rate.

In yet another aspect, the invention also provides a method of using the flow-through assay assembly and liquid handling device to identify an analytical target by loading a sample solution and a reagent onto a packed bed of the flow-through unit, aspirating unbound antigen and reagents such as enzyme conjugates through the unit, and identifying the analytical target of interest.

More specifically, the invention provides an apparatus comprising an assay unit and a multi-function hub. The assay unit comprises a packed bed, porous bed supports mounted in the assay unit at opposite ends of the packed bed, solid phase support beads located in the packed bed and having a selective-binding or reaction reagent mounted on their surface, an outlet from the assay unit having an outer perimeter and located below the packed bed, an inlet sealing surface adjacent to the packed bed, wherein the outer perimeter of the outlet from the assay unit is dimensioned to form a fluid-tight, friction seal with the inlet sealing surface when two assay units are nested, and an upper section dimensioned to form a friction contact with a probe or a second assay unit when two assay units are nested. The multi-function probe comprises a hub and a needle with a lumen disposed within the hub and extending from the hub, wherein the needle is dimensioned and configured to aspirate and dispense liquid directly and to form a fluid-tight liquid seal with the inlet sealing surface of the assay unit.

In some versions, the upper section of the assay unit and the hub are frusto-conical in shape.

In other versions, the upper section of the assay unit further comprises a raised set of ribs, the hub is dimensioned and configured to form a friction fit with the ribs of the assay unit, and the ribs of the assay unit define a channel between the upper section of the assay unit and the hub when the probe is inserted in the assay unit.

In other versions, the inlet sealing surface is dimensioned to form a fluid-tight, friction seal with a device selected from the group consisting of tubing having an outer diameter of from about 0.75 to about 1 mm and hypodermic needles having a gauge of from about 19 to about 21.

In other versions, the assay unit further comprises a chamber having a frusto-conical shape and positioned between the upper section and the inlet sealing surface.

In other versions, the hub forms a fluid-tight, friction seal with a proximal end of a pipet tip, wherein the multi-function probe is dimensioned and configured to aspirate and dispense liquid through the needle when the pipet tip is not attached to the hub and to aspirate and dispense liquid through the pipet tip when the pipet tip is attached to the hub.

In other versions, the apparatus further comprises a tubular probe shaft, a syringe pump, and a Cartesian robot, wherein the multi-function probe is mounted on the tubular probe shaft and is in fluid connection with the tubular probe shaft, the Cartesian robot controls movement of the tubular probe shaft and the attached multi-function probe in X, Y, and Z axes, and the syringe pump is configured to aspirate and dispense liquids through the multi-function probe.

In other versions, the apparatus further comprises a syringe barrel and a syringe plunger, wherein the multi-function probe is mounted on the syringe barrel and is in fluid connection with the syringe barrel, and the syringe plunger is configured to aspirate and dispense liquids through the multi-function probe.

In other versions, the apparatus further comprises a cylindrical extension mounted on the syringe plunger, wherein the cylindrical extension moveably fits into the lumen of the needle.

In other versions, the apparatus further comprises a support plate, an upper retaining plate, and a seal, wherein the support plate is disposed below the syringe barrel, the upper retaining plate is disposed above the syringe barrel, and the support plate and the upper retaining plate are configured to prevent movement of the syringe barrel in a vertical axis, and wherein the seal is connected to the needle within the syringe barrel, and the seal and the plunger are configured to prevent movement of the syringe barrel in a horizontal axis.

In other versions, the apparatus further comprises a wash manifold. The wash manifold itself may comprise a chimney, a suction chamber, and a plenum, wherein the chimney is dimensioned and configured to hold liquid and to fit the needle or the pipet tip within it, the suction chamber is configured to remove liquid from the chimney, and the plenum is configured to pump liquid into the chimney.

In other versions, the apparatus further comprises a stripper plate, used to strip assay units or pipet tips off probes.

In yet other versions, the invention comprises an automated liquid handling array. The automated liquid handling array may comprise two or more apparatuses. The apparatuses may be assembled in a one- or two-dimensional array and the syringe plungers may be coupled to a common drive plate. In some versions, the two-dimensional array may comprise an 8×12 array of 96 syringe barrels, which may be constructed to correspond to a standard 96-well microplate layout Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE SEVERAL VIEWS OF THE DRAWINGS

FIG. 2 is a cross-sectional schematic of a typical automated liquid handling probe of the prior art designed for aspirating and dispensing small volumes of liquid.

FIG. 3 is a cross-sectional schematic of a typical automated liquid handling probe of the prior art for use with disposable pipet tips, showing a tip mounted on the probe.

FIG. 4 is a cross-sectional schematic similar to FIG. 3, showing a mounted pipet tip device of the prior art with a packed bed in the distal end.

FIG. 5 is a cross-sectional schematic of a typical SPE-type packed bed device of the prior art, mounted on an automated liquid handling probe designed for use with pipet tips.

FIG. 6 is a cross-sectional schematic similar to FIG. 5, showing two SPE-type devices of the prior art connected in tandem (i.e., nested).

FIG. 7 is a cross-sectional schematic of an automated liquid handling probe of the current invention, showing the combined dispensing needle and hub for mounting pipet tips.

FIG. 8 is a cross-sectional schematic showing a pipet tip mounted on the probe shown in FIG. 7.

FIG. 9 is a cross-sectional schematic showing a flow-through assay unit mounted on the probe shown in FIG. 7.

FIG. 10 is a cross-sectional schematic of an automated liquid handling probe of the current invention, showing the details of its design.

FIG. 11A is a front elevation cross-sectional schematic of a flow-through assay unit of the present invention, showing the key features for interfacing with the automated liquid handling probe.

FIG. 11B is a top plan cross-sectional schematic of the flow-through assay unit shown in FIG. 11A.

FIG. 12A is a front elevation cross-sectional schematic of an automated liquid handling probe inserted into a flow-through assay unit, showing the key interfaces.

FIG. 12B is a top plan cross-sectional schematic of the automated liquid handling probe and flow-through assay unit shown in FIG. 12A.

FIG. 13 is a cross-sectional schematic of the automated liquid handling probe of the current invention inserted into a pipet tip, showing the sealing area.

FIG. 14 is a cross-sectional schematic of the automated liquid handling probe with two flow-through assay units stacked in tandem (i.e., nested) mounted on it.

FIG. 21 is a cross-sectional schematic of a probe needle being used to dispense liquid directly into a tube.

FIG. 22 is a cross-sectional schematic of a device similar to that shown in FIG. 21, but with a pipet tip disposed on the end of a probe to dispense liquid into a tube.

FIG. 23 is a cross-sectional schematic of an assay unit mounted on the probe syringe with liquid being aspirated through the packed bed from a well or tube.

FIG. 24 is a cross-sectional schematic depicting the removal of the assay unit from the probe with a stripper plate.

FIG. 25 is a cross-sectional schematic of a wash manifold designed to be mounted on the deck of a liquid handling system to wash the outside and inside of an assay unit or other pipetting device. Specifically shown is a chimney, which contains a hole leading to a suction chamber used for removing liquid from the chimney.

FIG. 26 is also a cross-sectional schematic of a wash manifold designed to be mounted on the deck of a liquid handling system to wash the outside and inside of an assay unit or other pipetting device. Specifically shown is a plenum used for pumping liquid into the chimney.

FIG. 27 is a cross-sectional schematic depicting dispensing liquid through a probe and a packed bed of an assay unit into a tube.

FIG. 28 is a cross-sectional schematic depicting dispensing liquid through a probe and two assay units attached in tandem (i.e., nested) into a tube.

DETAILED DESCRIPTION OF THE INVENTION

Figure 1:
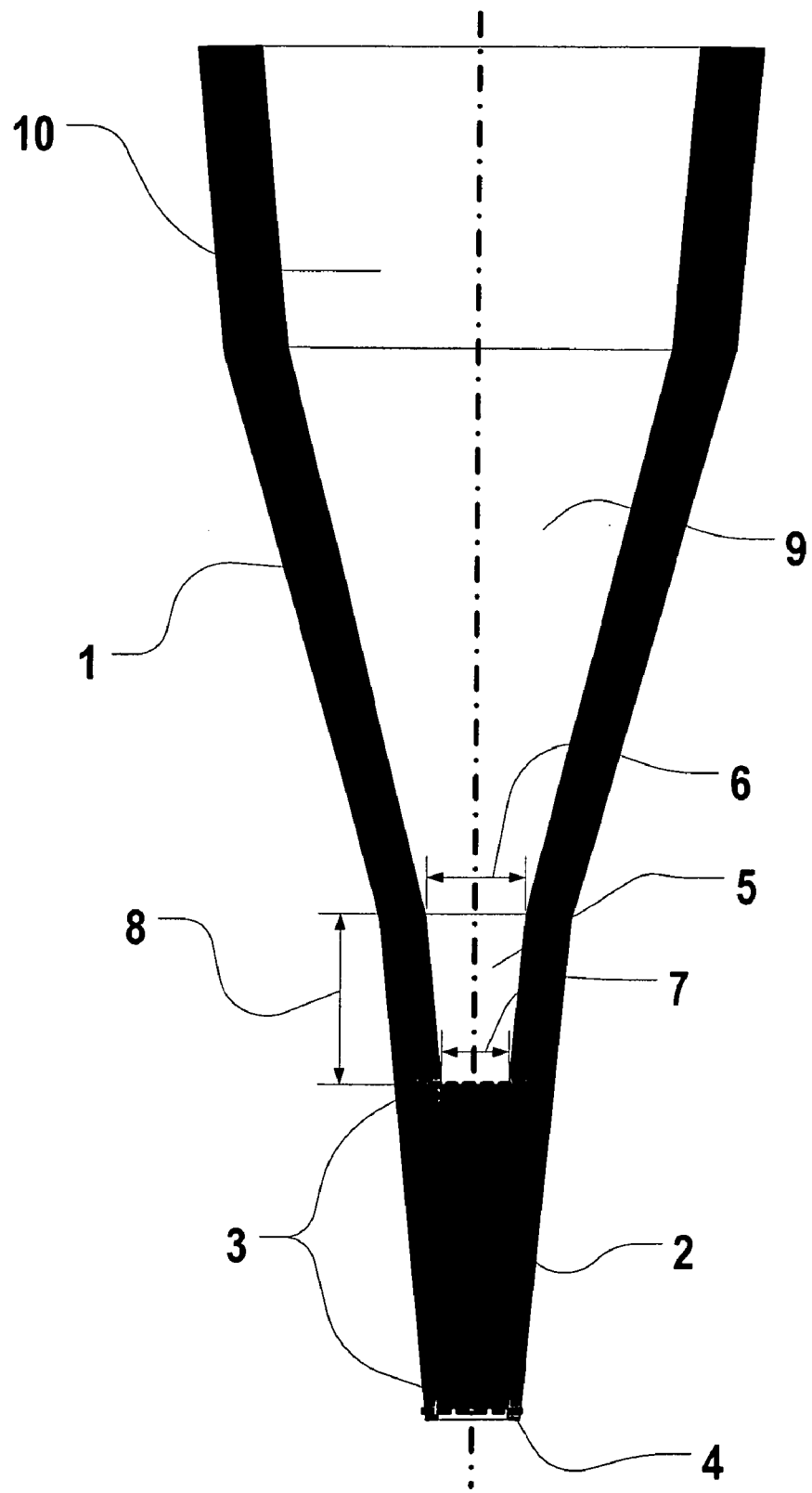
FIG. 1 is a cross-sectional schematic of a flow-through assay unit constructed according to an embodiment of the present invention.

Flow-Through Assay Unit:

An important element of this invention is a disposable flow-through assay unit which includes a packed bed of solid-phase adsorbent or immobilized-enzyme particles contained within a cylindrical or frustum-shaped chamber by inlet and outlet screens or filters. This device may be used in at least two major application areas—immunoassays (ELISA) and analytical sample preparation through purification and/or enzymatic treatment. A packed bed, flow-through assay unit of the present invention provides highly sensitive, rapid, and reproducible results for immunoassay and microliter-scale sample-prep applications, as described above, but can also be adapted to run large numbers of samples per day using typical automated liquid handling technology. In order to meet these requirements, the design of the assay unit itself, the nature of the liquid handling/pumping, and the interface between the liquid handler and the assay unit all had to be integrated in a novel way.

The use of a packed bed of solid-phase, non-porous adsorbent beads in the assay unit of the present invention reduces the diffusion path for binding of molecules in the sample to molecules immobilized on the surface to the order of microns (the space between the beads). Because of this, complete binding equilibrium can be reached with a residence time as brief as 30 seconds. This dramatically reduces the overall assay time (15-30 minutes vs. 4-24 hours) by eliminating long incubations. It also eliminates most of the sources of variability mentioned above because the binding reactions in each step actually reach completion, so the timing of the steps and control of mixing is not critical. Reagent addition (performed at a controlled flow rate through a packed bed of adsorbent particles rather than by incubation in a well) can be very reproducible with proper design of the pumps used. The most critical parameters controlling reproducibility are the measurement of the sample volume (all other reagents are added in excess, so volume control for them is less critical) and the flow rate of substrate addition. These can be easily controlled to a precision of well under 5% using standard instrumentation.

The same assay unit of the present invention can also be used in a micro-preparative mode to purify particular molecules of interest for other micro-scale analytical techniques such as MS. In this mode, a packed bed contains any of a number of different particulate adsorbents (including but not limited to porous or non-porous particles, made of materials such as polystyrene-divinylbenzene, polyacrylamide, agarose, cellulose, silica, alumina, zirconia, composites thereof, and the like) with immobilized binding molecules (including but not limited to antibodies, antigens, nucleic acids, hormones, cytokines, receptors, enzymes, and the like) or other selective surface chemistries (including but not limited to ion exchange, normal phase, reversed phase, hydrophobic interaction, gel filtration, affinity chromatography, mimetic ligand chromatography, metal chelate chromatography, and the like). Any of the above-mentioned binding molecules or selective surface chemistries, or any other similar reagents, may be used as selective-binding reagents with the present invention. In use, samples containing the target molecules are passed through the packed bed. The target molecules bind to the selective adsorbent particles, and non-binding contaminants are washed away. The bound target is then eluted using, for example, acid or a salt solution and collected into a tube or on a surface spot for further analytical processing. It is also possible to immobilize a reaction reagent such as an enzyme (including but not limited to proteases, kinases or glycosidases) to the packed bed to enable very rapid selective digestion or other processing of the target molecule as it passes through the packed bed at a controlled flow rate prior to further analysis.

The applications for which the assay unit of the present invention may be used are typically in the fields of life science research and pharmaceutical development. Samples in these fields are normally from biological systems or clinical patients. The sample volumes can be quite small (in the range of tens to hundreds of microliters), and are quite precious. In addition, many of the antibodies and other reagents used in the tests are expensive, so there is a strong desire to minimize the consumption per test. These factors drive toward minimizing the scale of the tests as much as possible. It is also important, however, to utilize industry-standard microplates, pipet tips, and other labware as much as possible. Complete automation of the analytical procedure is also a critical need.

FIG. 1 shows the assay unit 1 of the present invention. FIG. 1 depicts the general layout and key features of the assay unit 1, comprising a very small volume packed bed of particles 2. The packed bed 2 is contained within a cylindrical or frusto-conical reaction chamber or bed having a defined inlet and outlet sealed by a pair of porous bed supports 3. These bed supports may consist of any of a wide range of woven or non-woven screens, filters, or membranes made from polymer, metal, ceramic, or paper with an average pore size that is sufficient to contain the adsorbent particles. The outlet 4 from the packed bed chamber is located at or very close to the distal end of the assay unit 1, and the shape of the outer perimeter of the distal end is designed to be identical to the outer perimeter of the distal end of a standard 200 µL pipet tip, with an outer diameter of less than 1 mm.

The assay unit 1 is shaped so as to have three distinct frustum-shaped surfaces. The first, closest to the packed bed 2, is the inlet sealing surface 5. The inlet sealing surface 5 is frusto-conical in shape and has an inlet diameter 6, an outlet diameter 7, and a length 8 defined to enable either a tip or needle shaped similarly to a standard pipet tip or the outlet tip of another assay unit to form an air-tight and fluid-tight seal when inserted in the assay unit 1. The second surface, above the inlet sealing surface 5, is a chamber 9 serving as a spacer between the first and third surfaces. The chamber 9 has a volume designed to hold typical required amounts of samples or reagents, typically ranging from 5 to 100 µL so that the assay unit may be used as a spin column or in a vacuum manifold like a conventional SPE device. The third frusto-conical surface, adjacent to the proximal end of the assay unit 1, is the upper section 10. The upper section 10 is sized to fit on the distal end of a standard 200 µL laboratory pipet (i.e. is shaped identically to the proximal end of a standard 200 µL, pipet tip) but has venting means to prevent the formation of a liquid- or gas-tight seal on the pipet.

The dimensions of the inlet sealing surface 5 are critical for enabling the inlet of the packed bed 2 to be in fluid-tight connection to tips, probes, or needles used for accurately aspirating or dispensing microliter liquid volumes. FIG. 2 shows an example of a typical direct liquid handling probe 15 or needle with an outlet tip having an outer diameter (OD) in the range of 0.5-1.0 mm used for pipetting microliter liquid volumes. Hypodermic needles in the range of 19 to 21 gauge and pipet tips having a volume of from about 10 µL to about 200 µL are also used for pipetting microliter volumes and have similar outer diameter sizes at their tips. FIGS. 3, 4, 8, and 22, for example, show an example of a standard disposable 200 µL pipet tip 22 used for pipetting microliter volumes.

The inlet diameter 6 of the assay unit inlet sealing surface 5 is selected so that tips, probes, needles, or tubing having the sizes mentioned above will just fit into the upper portion of the inlet sealing surface 5 to form a fluid-tight seal. The inlet diameter 6 may be approximately at least 1 mm and is preferably in the range of 1.2 to 1.5 mm. The outlet diameter 7 is selected so that when the tip is inserted into the inlet sealing surface 5, it will form an interference seal before touching the inlet porous bed support 3, as shown in FIG. 9. This outlet diameter 7 is less than 0.8 mm and preferably in the range of 0.7 to 0.75 mm. The inlet sealing surface length 8 determines the angle between the walls of the inlet sealing surface 5. This angle must be slightly greater than the outer angle of the standard pipet tips 22 in order to form a reliable seal on the very end of the tips to prevent dead spaces and holdup of liquids between the pipet tip 22 and the inlet sealing surface 5. For commercially available pipet tips, the angle between the center axis and the wall of the inlet sealing surface 5 should be in the range of 5 to 7 degrees.

This type of sealing mechanism is highly reliable, despite only gentle force (1-3 lb) along the axis of the assay unit 1 being required to make or break the seal. Seals can easily be made by automated robotic systems, which aid in automating the entire assay process. Because of the very small diameters involved, the seals are capable of pressures in excess of 5 bar, even with just the friction of the interfering taper fit.

Prior Art Devices:

Many of the prior art devices designed to provide a small-volume packed bed for extraction of specific molecules from microliter-scale samples are based on the standard disposable pipet tip 22 (FIG. 3). With disposable pipet tips 22, an automated liquid handling probe 25 is used that is based on the standard Luer fitting used in medical syringes. These automated probes 25 typically have an outer diameter of at least 5 mm. Inserting the automated probe 25 into the proximal end 24 of a pipet tip 22 using axial force forms an air-tight seal with the proximal end 24 of the pipet tip 22. The air-tight seal enables the probe 25 to move air in or out of the tip, which in turns causes liquids to aspirate or dispense through the distal tip. Note that unlike the direct fluid handling system probe 15 shown in FIG. 2, the automated probe 25 is not suitable for directly aspirating or dispensing liquids because of its relatively large OD, which would cause large liquid drops to adhere to the tip. Thus, it can only be used with pipet tips 22.

When a packed bed 2 is placed in the end of the pipet tip, as seen in FIG. 4, the air displacement will cause liquids to be aspirated or dispensed through the bed, exposing the liquid to adsorbent particles comprising the packed bed 2. A number of prior art inventions (see for example Gjerde et al. (WO 2004/007081) and Kopaciewicz et al., *Journal of Chromatography*, 519:1 (1990), incorporated herein by reference), have taught devices of this type with various means for holding the adsorbent particles in place in the tip. All of them have only one port (the distal tip) for moving liquid into and out of the bed, so each aliquot of liquid must be both aspirated and dispensed, usually multiple times, to either bind or elute a target molecule. This causes uniform mixing of the liquid aliquot and the subsequent loss of any chromatographic resolution created by the packed bed.

One major problem with this approach is that liquids are moved through the packed bed by pressure changes caused by air displacement. Because air is compressible, the system is not "hydraulically hard," and small differences between the flow resistance of the packed bed or bed supports between individual devices or between the viscosities of different liquids will cause differences in the liquid flow rate. In addition, as the liquid flows into or out of the tip, the volume of air changes, causing changes in the pressure and thus the flow rate. Thus, with this type of device it is impossible to control the flow rate with any precision. This leads to wide potential variability in binding or recovery, even in simple binding/elution procedures. For immunoassays in a packed bed device, the degree of colored or fluorescent product formation for a given amount of bound enzyme is inversely proportional to the substrate flow rate, so changes in the flow rate will change the final result significantly. Air displacement-type pipet tip devices are thus not suitable at all for immunoassay applications.

Solid phase extraction (SPE) devices are another approach. Many SPE devices are based on syringe barrels with frits inserted to retain the packed bed. These are typically used with vacuum manifolds to drive liquids through and so have no direct flow rate control. They are also relatively large volume and are poorly suited for microliter scale samples. Some SPE devices are designed to interface with smaller probe tips or needles. The SPE device of Gamble et al. (U.S. Pat. No. 7,001,774, incorporated herein by reference), uses a septum to provide a seal with a hypodermic needle of a syringe or probe and thus can provide good flow control. However, this device does not provide any means for the automated liquid handler to utilize pipet tips for general liquid handling. The SPE device 26 of Cook et al. (U.S. Pat. No. 6,761,855, incorporated herein by reference) (FIG. 5), has a female Luer-type inlet (designed to interface with a pipet tip or male Luer-type probe 25) and a male Luer outlet 27 (designed to connect with a second SPE device of the same type, as shown in FIG. 6). The Luer connections on this device are rather large relative to the microliter samples used in many assays and are thus poorly suited for direct aspiration or dispensing of small volumes.

Multi-Function Liquid Handling Probe for Use with Assay Unit:

Another key element of the current invention is a multi-function probe for use in an automated liquid handling system dimensioned and configured to perform three distinct functions: 1) directly aspirate or dispense microliter fluid volumes; 2) operate with standard disposable pipet tips; and 3) interface with the flow-through assay units of the current invention, also described in U.S. patent application Ser. No. 11/188,535. These three functions can be performed while providing high precision control of the flow rate and volume. The ability of the multi-function probe to directly handle small volumes by itself is very useful for directly dispensing or diluting samples and reagents, and for picking up liquids for directly dispensing them into the assay unit. In cases where carry-over between samples is less critical (such as for dispensing buffers for dilution), direct liquid handling also eliminates the need to use pipet tips and the consequent generation of solid waste. In cases where prevention of carry-over between samples is highly critical (such as with very sensitive immunoassays) the use of standard pipet tips enables the liquid handling system to perform general functions such as aliquotting and diluting in addition to operating the assay units.

FIG. 7 shows the general design of a probe of the current invention. A hub 23 with diameter suitable for sealing to pipet tips is connected above a straight or tapered needle 21. The needle 21 and hub 23 are dimensioned so that the probe can aspirate or dispense microliter volumes in a manner similar to a standard direct probe 15, as shown in FIG. 2, or with a pipet tip 22, as shown in FIG. 3. When a pipet tip is not mounted on the probe, as is shown in FIG. 7, the probe may handle fluids through the needle 21 in the same manner as a standard direct probe. When a pipet tip 22 is mounted on the probe, as shown in FIG. 8, the hub 23 forms a seal at the proximal end of the tip 22, enabling pipetting through air displacement. When an assay unit 1 is mounted on the probe, as shown in FIG. 9, the distal end of the needle 21 of the probe engages the inlet sealing surface 5 of the assay unit 1, forming a fluid-tight seal with the packed bed.

FIG. 10 shows a more detailed view of a design for a multi-function probe 30. In this design, a straight or tapered-tip needle 31 fits tightly into a hole in a hub 32. The hub may comprise a frusto-conical section designed to seal on a pipet tip. FIG. 11A shows a detailed view of an assay unit 1 designed to work with the probe 30 of FIG. 10. The key features of the assay unit 1 which interface with the multi-function probe 30 are the inlet sealing surface 5 located immediately above the packed bed 2 and the upper section 10 at the inlet of the assay unit. As seen in FIGS. 11A and 11B, the upper section 10 contains a set of raised ribs 34, which form channels to provide venting of air around the probe, thus preventing the formation of a seal. FIGS. 12A and 12B show the probe 30 of FIG. 10 inserted into the assay unit 1 of FIGS. 11A and 11B. The end of the needle 31 of the probe 30 forms a tapered interference seal with the inlet sealing surface 5 of the assay unit 1. The assay unit ribs 34 provide a friction fit with the probe hub 32. With the probe 30 inserted into the assay unit 1, the ribs 34 define channels 35 between the probe hub 32 and the assay unit upper section 10. The channels 35 serve as vents so that the interface between the probe hub 32 and the assay unit upper section 10 does not create an air-tight seal.

Having a firm friction fit between the assay unit upper section 10 and the probe hub 32 is critical for holding the assay unit securely on the probe during operation. However, if the assay unit upper section 10 were to form an air-tight seal on the probe similar to the seal formed between a conventional automated probe 25 and a pipet tip 22 (as shown in FIGS. 3 and 4), a significant amount of air (relative to the packed bed volume) would be pushed downward into the assay unit as the probe is inserted (or would be pulled upward through the assay unit as the probe is removed). This would in turn expel all the liquid in the packed bed and trap air in the bed, degrading the performance dramatically. The venting provided by the ribs 34 and in the upper section 10 of the assay unit prevents this "air pistoning effect" when connecting to a probe 30, while still providing a secure fit.

Because the ribs 34 are on the assay unit 1 and not the probe 30, the probe 30 creates a seal when connected to a pipet tip. The seal is established through connections with the pipet tip 22 and the hub 32 of the probe 30, as shown in FIG. 13, enabling pipetting with the pipet tip.

Another important feature of both the assay unit and corresponding multi-function system probe is that the devices are dimensioned so that two assay units 1 may be connected in tandem (i.e., nested) as shown in FIG. 14, so that the outlet tip of the upper assay unit 1 is sealed in the inlet sealing surface 5 of the lower assay unit 1. This configuration enables microliter quantities of liquid to be transferred from one assay unit to another (by either aspirating or dispensing) with essentially no fluid loss. This mode of operation places constraints on the relative dimensions of the probe 30, the probe needle 31 and the position of the inlet sealing surface 5 and outlet tips of the assay unit itself.

Figure 15A:
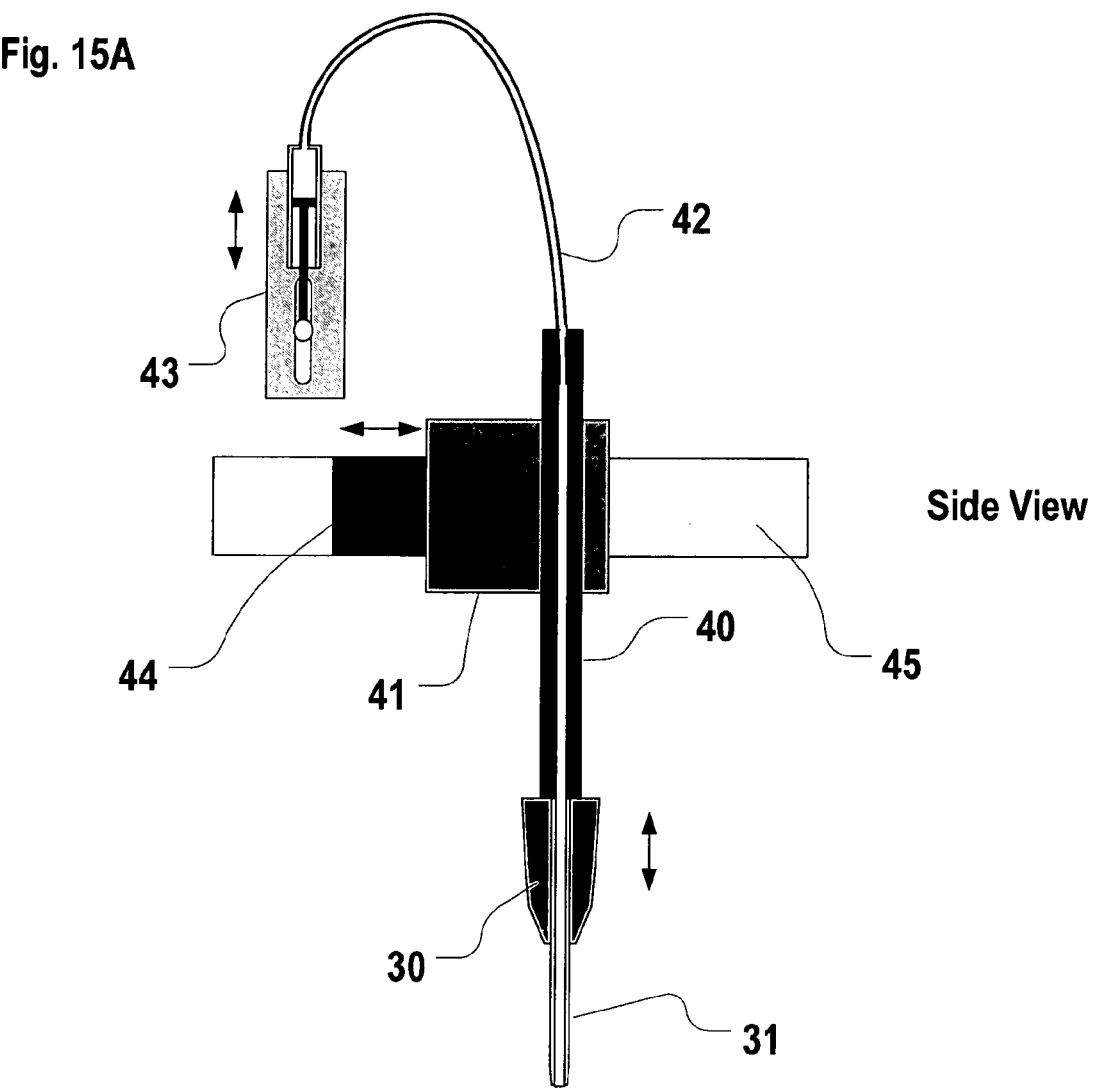
FIG. 15A is a front elevation, partial cutaway representation of an automated liquid handling probe of the current invention mounted on a conventional X/Y/Z liquid handling system and connected to a syringe pump by tubing.
Figure 15B:
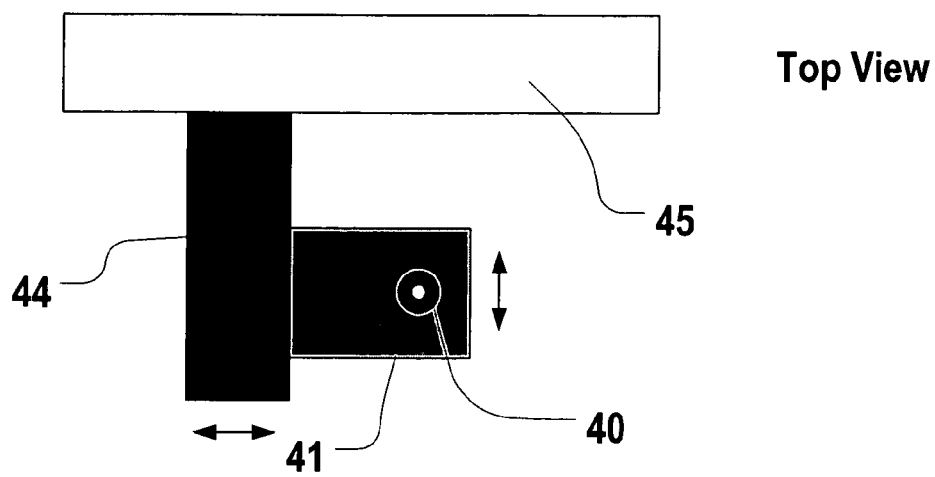
FIG. 15B is a top plan view of the automated liquid handling probe and conventional X/Y/Z liquid handling system shown in FIG. 15A.

Liquid Handling Systems for the Multi-Function Probe and Assay Unit:

One embodiment of an automated liquid handling system using a multi-function system probe and assay unit of the current invention is shown in FIGS. 15A and 15B. This is a typical Cartesian (X/Y/Z) robot with the multi-function probe 30 mounted on a tubular probe shaft 40, driven up and down in the Z direction by a linear actuator 41. The probe needle 31 connects to a liquid channel in the probe shaft, which in turn is connected by flexible tubing 42 to a syringe pump 43 for aspirating and dispensing controlled volumes of liquid through the probe. The Z actuator 41 is moved on a Y actuator 44, which in turn is moved on an X actuator 45 to provide full motion of the probe over the entire volume of the system deck. This type of automated liquid handling system is currently in use in many laboratories, and the addition of the multi-function probe tip 30 enables such a system to be used for handling liquid directly, with disposable pipet tips, or with the assay units of the current invention.

A potential limitation for some applications with the type of system shown in FIGS. 15A and 15B is that the combined probe 30, probe shaft 40, and tubing system 42 has a considerable volume (usually several milliliters), which is much greater than the typical sample or reagent volume, which is in the tens or hundreds of microliters. In such a long run of tubing, it is common to trap air bubbles, which give the system varying degrees of hydraulic compliance, reducing the accuracy and precision of flow and volume control. The compliance of the flexible tubing itself also is a potential limitation.

Another potential limitation with the type of system shown in FIGS. 15A and 15B stems from the need in some applications to run many assay units in parallel in order to increase sample throughput. For many applications, users need to run very large numbers of immunoassays or sample-preparation procedures per day, and in many fields, the throughput demands are increasing. Thus, it is important to be able to provide a large number of parallel pumping channels for driving assay units. The type of liquid handling system shown in FIGS. 15A and 15B is limited in the number of individual probes or pumping channels that can be provided, which is typically around eight.

Figure 16:
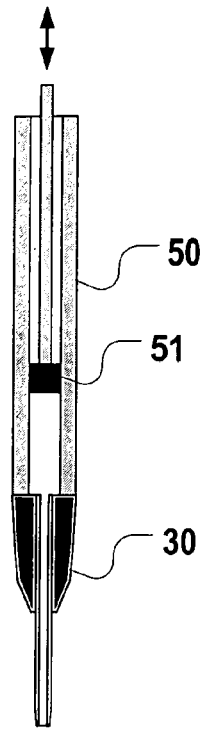
FIG. 16 is a cross-sectional schematic of an automated liquid handling probe of the current invention directly connected to a syringe.
Figure 20:
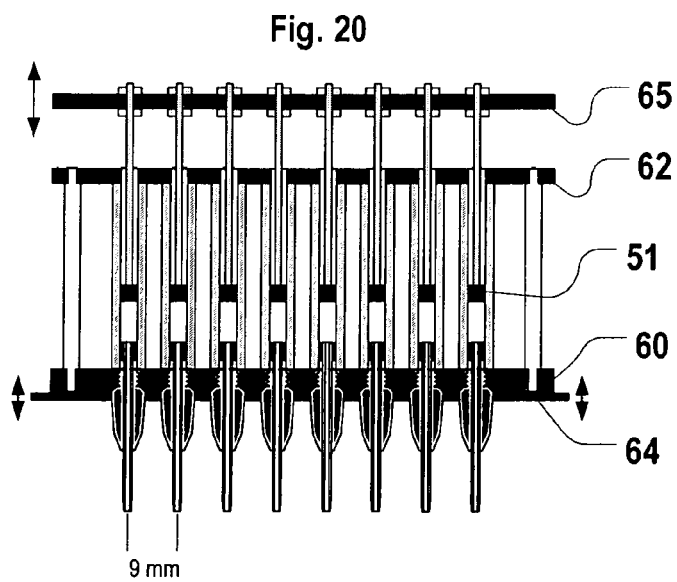
FIG. 20 is a cross-sectional representation of a multi-channel liquid handling head with a single syringe drive incorporating syringes and probes of the current invention.

In order to overcome this limitation, the multi-function probe 30 can be directly mounted on a syringe barrel 50, as shown in FIG. 16. A drive must be provided to move the syringe plunger 51 up and down in order to directly aspirate and dispense liquids through the probe. This "probe syringe" device has essentially no hydraulic compliance, and is small enough that multiple devices can be mounted in a single drive (as shown in FIG. 20), easily providing, for example, 96 pumping channels for processing an entire 96-well microplate of samples at a time.

Figure 17:
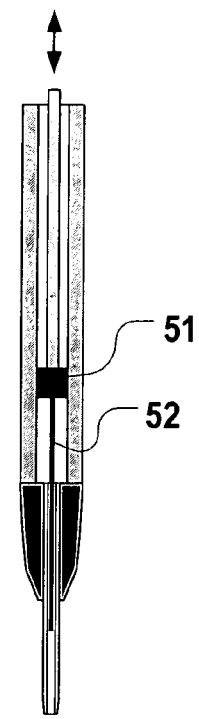
FIG. 17 is a cross-sectional schematic of an automated liquid handling probe similar to that shown FIG. 16 but with an extension of the syringe plunger to eliminate most of the dead volume in the probe needle.

Because the probe syringe in the device shown in FIG. 16 is operated in an inverted position, it is difficult to expel all the air from the syringe. Also, the volume of liquid contained in the probe needle is difficult to completely wash out in order to minimize carryover between samples. These problems may be largely solved by the addition of a cylindrical extension 52 on the end of the syringe plunger 51, as shown in FIG. 17. The extension 52 fits with some clearance into the lumen of the needle but takes up most of the volume of the needle, greatly reducing the entrapped air and enhancing washout of the syringe.

Figure 18:
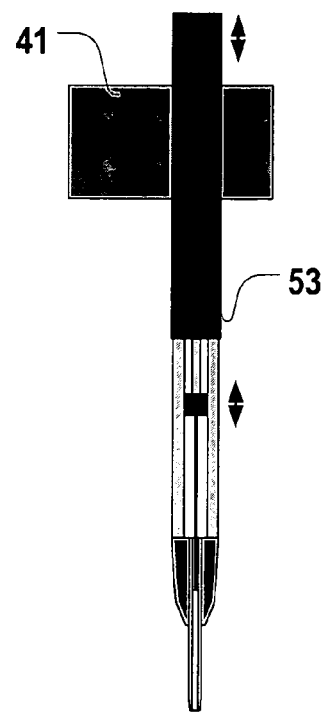
FIG. 18 is a schematic representation of the probe and syringe shown in FIG. 17 mounted on a small diameter syringe drive, which is in turn mounted on an X/Y/Z robotic actuator to form a complete liquid handling system.

As shown in FIG. 18, the multi-function probe syringe device may be mounted on a small diameter drive system 53 for the syringe plunger 51, similar to that described by Londo et al. (U.S. Pub. No. 2008/0156117, incorporated herein by reference). Such a device can be moved in the Z direction individually by various Z actuators 41, as shown in FIG. 18, or arranged with other devices to form multi-channel systems. Additionally, such systems may be configured with X and Y actuators 45,44 (shown in FIGS. 15A and 15B) to form an automated system.

Figure 19:
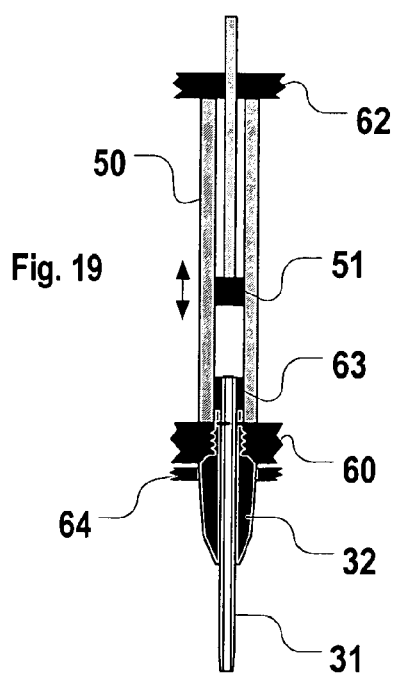
FIG. 19 is a cross-sectional schematic showing a syringe with a probe of the present invention for use in a multi-channel liquid-handling head.

FIG. 19 shows a modified design for a multi-function probe syringe of the current invention that is adapted for incorporating into a multi-channel head with a single, common drive for all the syringes. The probe hub 32 is modified to include threads for mounting into a support plate 60. The probe needle 31 extends through the hub on the top, and is modified to accept a seal 63 inside the syringe barrel 50. The barrel 50 is sandwiched between the support plate 60 and an upper retaining plate 62, which contains a hole for the syringe plunger 51 that is concentric with the inner diameter of the syringe barrel 50. The support plate 60 and upper retaining plate 62 prevent the syringe barrel 50 from moving in a vertical axis as the plunger 51 is moved, and the combination of the syringe plunger 51 and static needle seal 63 constrain the barrel from moving in horizontal axes. Otherwise, the barrel is free-floating. The free-floating barrel 50 is effectively self-aligning, preventing problems with syringe breakage which occur in conventional syringe pumps if the plunger shaft and barrel mounting are not perfectly aligned. A stripper plate 64 is mounted below the support plate 60, and contains holes through which the probe hubs 32 can pass. The stripper plate 64 is used to strip assay units or pipet tips off of the probes.

The design in FIG. 19 can be manufactured and assembled in one- or two-dimensional arrays, a cross section of which is shown in FIG. 20. If the total syringe unit is less than 9 mm in diameter, an 8×12 array of 96 syringe barrels may be constructed to correspond to a standard 96-well microplate layout. The syringe plungers 51 are coupled to a common drive plate 65, which in turn would be coupled to an actuator to drive all the syringes at once.

Method of Operating the Assay Unit:

FIGS. 21-28 show the various key functional operations of an assay unit and a multi-functional probe. In all cases, a syringe with an integrated probe 30, a preferred embodiment as depicted in FIG. 19, is shown.

FIG. 21 shows the probe needle 31 being used to dispense liquid directly into a well or tube 70 with a compression of the plunger 51. One key dimensional constraint for the probe 30 is that the needle 31 must be long enough to reach the bottom of common types of tubes or microplate wells. The most constrictive is the 384 well plate, in which wells are typically 11.4 mm deep and 3.6 mm wide at the top. Another critical container is the 0.2 mL PCR tube, which is typically 20 mm deep and 5.3 mm wide at the top. Both the probe 30 and assay unit 1 must meet these constraints, as shown in FIGS. 21 and 27.

In cases where carryover is a critical concern, a pipet tip 22 may be used to transfer liquids in the system, as shown in FIG. 22. In many procedures, it is advantageous to transfer a dilution buffer using the probe directly and the sample itself with a pipet tip.

FIG. 23 shows an assay unit 1 mounted on the probe 30 with liquid being aspirated from a well or tube 70 through the packed bed 2 into the probe needle 31 with an extension of the plunger 51. The volume and the flow rate of liquid may be controlled very precisely down to the microliter and microliter per minute range (or less), respectively, using this system. This type of step is used to apply reagents or samples to the packed bed 2, enabling a binding interaction or enzymatic reaction between molecules in the sample and molecules immobilized on the surface of the adsorbent beads.

After some steps, it may be necessary to remove the assay unit or pipet tip from the probe. This is done as shown in FIG. 24 by actuating the stripper plate 64, which pushes down on the top of the assay unit 1, driving it off the probe. If the tip of the assay unit 1 is inserted into a hole in a storage rack when stripped, the assay unit 1 may be remounted on the probe for use in subsequent steps. Alternatively, at the end of the procedure the assay unit 1 can be ejected into a waste container.

In virtually all analytical procedures, a critical operation is to wash away unbound molecules and excess liquid (sample or reagent) from both the outside of the assay unit and from the packed bed itself. Complete washing is vital to insure that only molecules that are specifically bound to the adsorbent beads are carried through to the next step of the procedure. FIG. 25 shows a wash manifold 71 configured to be mounted on the deck of the liquid handling system to wash both the outside and inside of the assay units. The manifold 71 has mounted in it a "chimney" 72 which is configured to fit the outside of assay units and have a hole through the side connecting to a suction chamber 73, which in turn is connected through a valve to a vacuum waste suction device. When the suction is activated, liquid in the chimney is pulled to waste. This allows for removal of liquid expelled from the syringe with compression of the plunger 51. The liquid may be expelled either through an assay unit, as shown, or directly from the probe needle, as both have similar profiles and dimensions that enable it to fit into the chimney 72.

As shown in FIG. 26, the chimney 72 also has a hole through the bottom which connects to a plenum 74, which in turn is connected to a pump for pumping various wash liquids into the chimney 72. By alternately pumping liquid into the chimney 72 and suctioning it out (as shown in FIG. 25), the outside of the assay units can be effectively washed. Once this is accomplished, the wash liquid can be left in the chimney 72 and aspirated up through the packed bed with extension of the plunger 51, which in turn washes the packed bed itself.

The final step in virtually all assay procedures is to dispense liquid from the syringe through the packed bed of the assay unit 1 into a well or tube 70, as shown in FIG. 27, for final analysis in an optical plate reader, mass spectrometer, HPLC, capillary electrophoresis system or other analytical instrument. The liquid is dispensed by compressing the plunger 51. In an immunoassay, this final step comprises pumping enzyme substrate through the assay unit and collecting the colored or fluorescent product of the enzyme reaction as a means of measuring the amount of analyte present in the original sample. In sample prep separations (such as for a mass spectrometer), the bound and purified target analyte is typically eluted off the packed bed using acid, salt or other elution buffers, and collected in the well or tube or on a plate for analysis in the instrument.

In some cases, additional separation or treatment steps are needed that can be performed on an assay unit packed with different adsorbent beads. This can be done by stacking the assay units 1 in tandem as shown in FIG. 28. This mode of operation is useful for several applications. One application would be to combine multiple separation steps on an automated system. For example, the upper assay unit could contain an ion exchange packing to selectively bind and purify the target from a complex sample such as blood serum or cell culture supernatant. Elution from this packing is through the use of a high concentration of salt, which is not compatible with mass spectrometry. If the lower assay unit contains a reversed-phase packing, when the target is eluted from the upper assay unit into the lower assay unit it will be bound on the reversed phase packing. After the assay units are decoupled, the salt can be washed away, and the target eluted from the lower assay unit using an organic solvent solution that is compatible with the mass spectrometer.

A second type of application for the tandem stacked mode of operation is the use of an immobilized protease, such as trypsin, in the lower assay unit. During passage of a sample aliquot aspirated in the upward direction through the lower assay unit, the proteins present would be digested by the immobilized enzyme into defined peptides. By using immobilized enzyme, a much higher amount of enzyme can be used than is normally employed in the solution phase, giving rise to a faster digestion with no chance of autolysis products from the enzyme contaminating the analysis. If a reversed phase packing is used in the upper unit, the digested peptides would be captured and concentrated, and any salt required in the digestion buffer would be removed by washing after the units are decoupled. The peptides could then be eluted in an organic solvent solution that is compatible with the mass spectrometer.

We claim:
1. An apparatus comprising:
   an assay unit comprising:
     a packed bed;
     porous bed supports mounted in the assay unit at opposite ends of the packed bed;
     solid phase support beads located in the packed bed and having a selective-binding or reaction reagent mounted on their surface;
     an outlet from the assay unit having an outer perimeter and located below the packed bed;
     an inlet sealing surface adjacent to the packed bed;
     an upper section having an inside surface dimensioned to form a friction contact with an outside surface of a probe hub, and further comprising at least one raised rib extending from the inside surface of the upper section, wherein the rib defines at least one gap between the inside surface of the upper section and the outside surface of the probe hub to provide venting of air around the probe hub, and to prevent creating an air-tight seal between the upper section and the probe hub;
   a multi-function probe comprising:
     a hub;
     a needle with a lumen disposed within the hub and extending from it, wherein the needle is dimensioned and configured to aspirate and dispense liquid directly and to form a fluid-tight liquid seal with the inlet sealing surface of the assay unit.

2. The apparatus of claim 1, wherein the inlet sealing surface is dimensioned to form a fluid-tight, friction seal with a device selected from the group consisting of tubing having an outer diameter of from about 0.75 to about 1 mm and hypodermic needles having a gauge of from about 19 to about 21.

3. The apparatus of claim 1, further comprising a chamber having a frusto-conical shape and positioned between the upper section and the inlet sealing surface.

4. The apparatus of claim 1, wherein the hub forms a fluid-tight, friction seal with a proximal end of a pipet tip, wherein the multi-function probe is dimensioned and configured to aspirate and dispense liquid through the needle when the pipet tip is not attached to the hub and to aspirate and dispense liquid through the pipet tip when the pipet tip is attached to the hub.

5. The apparatus of claim 4, further comprising a tubular probe shaft, a syringe pump, and a Cartesian robot, wherein the multi-function probe is mounted on the tubular probe shaft and is in fluid connection with the tubular probe shaft, the Cartesian robot controls movement of the tubular probe shaft and the attached multi-function probe in X, Y, and Z axes, and the syringe pump is configured to aspirate and dispense liquids through the multi-function probe.

6. The apparatus of claim 5, wherein the upper section of the assay unit further comprises a raised set of ribs, the upper section of the hub is dimensioned and configured to form a friction fit with the ribs of the assay unit, and the ribs of the assay unit define a gap between the upper section of the assay unit and the hub when the probe is inserted in the assay unit.

7. The apparatus of claim 5, wherein the inlet sealing surface is dimensioned to form a fluid-tight, friction seal with a device selected from the group consisting of tubing having an outer diameter of from about 0.75 to about 1 mm and hypodermic needles having a gauge of from about 19 to about 21.

8. The apparatus of claim 5, further comprising a chamber having a tirusto-conical shape and positioned between the upper section and the inlet scaling surface.

9. The apparatus of claim 4, further comprising a syringe barrel and a syringe plunger, wherein the multi-function probe is mounted on the syringe barrel and is in fluid connection with the syringe barrel, and the syringe plunger is configured to aspirate and dispense liquids through the multi-function probe.

10. The apparatus of claim 9, further comprising a cylindrical extension mounted on the syringe plunger, wherein the cylindrical extension moveably fits into the lumen of the needle.

11. The apparatus of claim 9, wherein the upper section of the assay unit further comprises a raised set of ribs, the upper section of the hub is dimensioned and configured to form a friction fit with the ribs of the assay unit, and the ribs of the assay unit define a gap between the upper section of the assay unit and the upper section of the hub when the probe is inserted in the assay unit.

12. The apparatus of claim 9, wherein the inlet sealing surface is dimensioned to form a fluid-tight, friction seal with a device selected from the group consisting of tubing having an outer diameter of from about 0.75 to about 1 mm and hypodermic needles having a gauge of from about 19 to about 21.

13. The apparatus of claim 9, further comprising a chamber having a frusto-conical shape and positioned between the upper section and the inlet sealing surface.

14. The apparatus of claim 11, further comprising a support plate, an upper retaining plate, and a seal, wherein the support plate is disposed below the syringe barrel, the upper retaining plate is disposed above the syringe barrel, and the support plate and the upper retaining plate are configured to prevent movement of the syringe barrel in a vertical axis, and wherein the seal is connected to the needle within the syringe barrel, and the seal and the plunger are configured to prevent movement of the syringe barrel in a horizontal axis.

15. The apparatus of claim 14, further comprising a wash manifold comprising a chimney, a suction chamber, and a plenum, wherein the chimney is dimensioned and configured to hold liquid and to fit the needle or the pipet tip within it, the suction chamber is configured to remove liquid from the chimney, and the plenum is configured to pump liquid into the chimney.

16. The apparatus of claim 14, further comprising a stripper plate.

17. An automated liquid handling array comprising two or more apparatuses as claimed in claim 14, wherein the apparatuses are assembled in a one- or two-dimensional array and the syringe plungers are coupled to a common drive plate.

18. An apparatus comprising:
an assay unit comprising:
  a packed bed;
  porous bed supports mounted in the assay unit at opposite ends of the packed bed;
  solid phase support beads located in the packed bed and having a selective-binding or reaction reagent mounted on their surface;
  an outlet from the assay unit having an outer perimeter and located below the packed bed;
  an inlet sealing surface adjacent to the packed bed, having a frusto-conical shape, and dimensioned to form a fluid-tight, friction seal with a device selected from the group consisting of tubing having an outer diameter of from about 0.75 to about 1 mm and hypodermic needles having a gauge of from about 19 to about 21;
  an upper section having a frusto-conical inside surface, and further comprising at least one raised rib extending from the inside surface of the upper section, wherein the rib defines at least one gap between the inside surface of the upper section and the outside surface of the probe hub to provide venting of air around the probe hub, and to prevent creating an airtight seal between the upper section and the probe hub or second assay unit;
a multi-function probe comprising:
  a frusto-conical hub;
  a needle with a lumen disposed within the hub and extending from it, wherein the needle is dimensioned and configured to aspirate and dispense liquid directly and to form a fluid-tight liquid seal with the inlet sealing surface of the assay unit.

19. The apparatus of claim 18, further comprising a chamber having a frusto-conical shape and positioned between the upper section and the inlet sealing surface.

* * * * *

UNITED STATES PATENT AND TRADEMARK OFFICE
CERTIFICATE OF CORRECTION

| | | |
|---|---|---|
| PATENT NO. | : 8,124,028 B2 | Page 1 of 1 |
| APPLICATION NO. | : 12/808833 | |
| DATED | : February 28, 2012 | |
| INVENTOR(S) | : Scott P. Fulton et al. | |

It is certified that error appears in the above-identified patent and that said Letters Patent is hereby corrected as shown below:

In column 17, line 33, in Claim 7, delete "scaling" and insert -- sealing --, therefor.

In column 17, line 40, in Claim 8, delete "tirusto-conical" and insert -- frusto-conical --, therefor.

In column 17, line 41, in Claim 8, delete "scaling" and insert -- sealing --, therefor.

Signed and Sealed this
Seventeenth Day of April, 2012

David J. Kappos
*Director of the United States Patent and Trademark Office*